United States Patent
Wakayama

(10) Patent No.: US 11,759,483 B2
(45) Date of Patent: Sep. 19, 2023

(54) METHOD FOR IMPROVING EYE CONDITIONS

(71) Applicant: LAIMU CORPORATION, Yokohama (JP)

(72) Inventor: Sachio Wakayama, Yokohama (JP)

(73) Assignee: LAIMU CORPORATION, Kanagawa (JP)

( * ) Notice: Subject to any disclaimer, the term of this patent is extended or adjusted under 35 U.S.C. 154(b) by 0 days.

(21) Appl. No.: 18/048,980

(22) Filed: Oct. 24, 2022

(65) Prior Publication Data
US 2023/0256031 A1  Aug. 17, 2023

Related U.S. Application Data

(63) Continuation of application No. 17/933,534, filed on Sep. 20, 2022.

(30) Foreign Application Priority Data

Feb. 14, 2022  (JP) ................................. 2022-020138

(51) Int. Cl.
| | | |
|---|---|---|
| *A61K 35/57* | (2015.01) | |
| *A61K 31/185* | (2006.01) | |
| *A61K 9/48* | (2006.01) | |
| *A61K 31/728* | (2006.01) | |
| *A61K 9/00* | (2006.01) | |
| *A61P 27/02* | (2006.01) | |
| *A61K 31/198* | (2006.01) | |
| *A61K 31/661* | (2006.01) | |
| *A61K 31/4172* | (2006.01) | |
| *A61K 31/197* | (2006.01) | |

(52) U.S. Cl.
CPC ............ *A61K 35/57* (2013.01); *A61K 9/0053* (2013.01); *A61K 9/4825* (2013.01); *A61K 31/185* (2013.01); *A61K 31/197* (2013.01); *A61K 31/198* (2013.01); *A61K 31/4172* (2013.01); *A61K 31/661* (2013.01); *A61K 31/728* (2013.01); *A61P 27/02* (2018.01)

(58) Field of Classification Search
None
See application file for complete search history.

(56) References Cited

U.S. PATENT DOCUMENTS

2019/0046587 A1  2/2019  Wakayama et al.

FOREIGN PATENT DOCUMENTS

| JP | H07241200 A | 9/1995 |
|---|---|---|
| JP | 2002145800 A | 5/2002 |
| JP | 2011042632 A | 3/2011 |
| JP | 2017088545 A | 5/2017 |
| JP | 2019006708 A | 1/2019 |
| JP | 2019038783 A | 3/2019 |
| JP | 2019052123 A | 4/2019 |

OTHER PUBLICATIONS

Raskin et al. (2004) Current Pharmaceutical Design 10, 3419-3429. (Year: 2004).*
Revilla et al. (1998) J. Agric. Food Chem. 46, 4592-4597. (Year: 1998).*
Office Action dated Mar. 29, 2022 issued in the corresponding Japanese Patent Application No. 2022-020138 with its English machine Translation.
Office Action dated Jun. 7, 2022 issued in the corresponding Japanese Patent Application No. 2022-020138 with its English machine Translation.
Terashita et al. "Chemical composition of low-molecular weight hyaluronic acid from comb (chicken) and maintaining the moisture effect of skin by a clinical test" Memoirs of the Faculty of Agriculture of Kinki University, 44, pp. 1-8 (2011)—English Abstract attached.
Fancl, Nanoized Hyarulonic Acid, 2011; downloaded from https://www.fancl.jp/news/pdf/2011_1216_nanokahiaruronsan.pdf.

* cited by examiner

*Primary Examiner* — Russell G Fiebig
(74) *Attorney, Agent, or Firm* — BROWDY AND NEIMARK, PLLC

(57) ABSTRACT

Disclosed is a method for improving eye conditions comprising orally administering to humans, an ethanol-soluble component-containing degradation product obtained by degrading a comb with a protease and removing a solid.

7 Claims, 1 Drawing Sheet

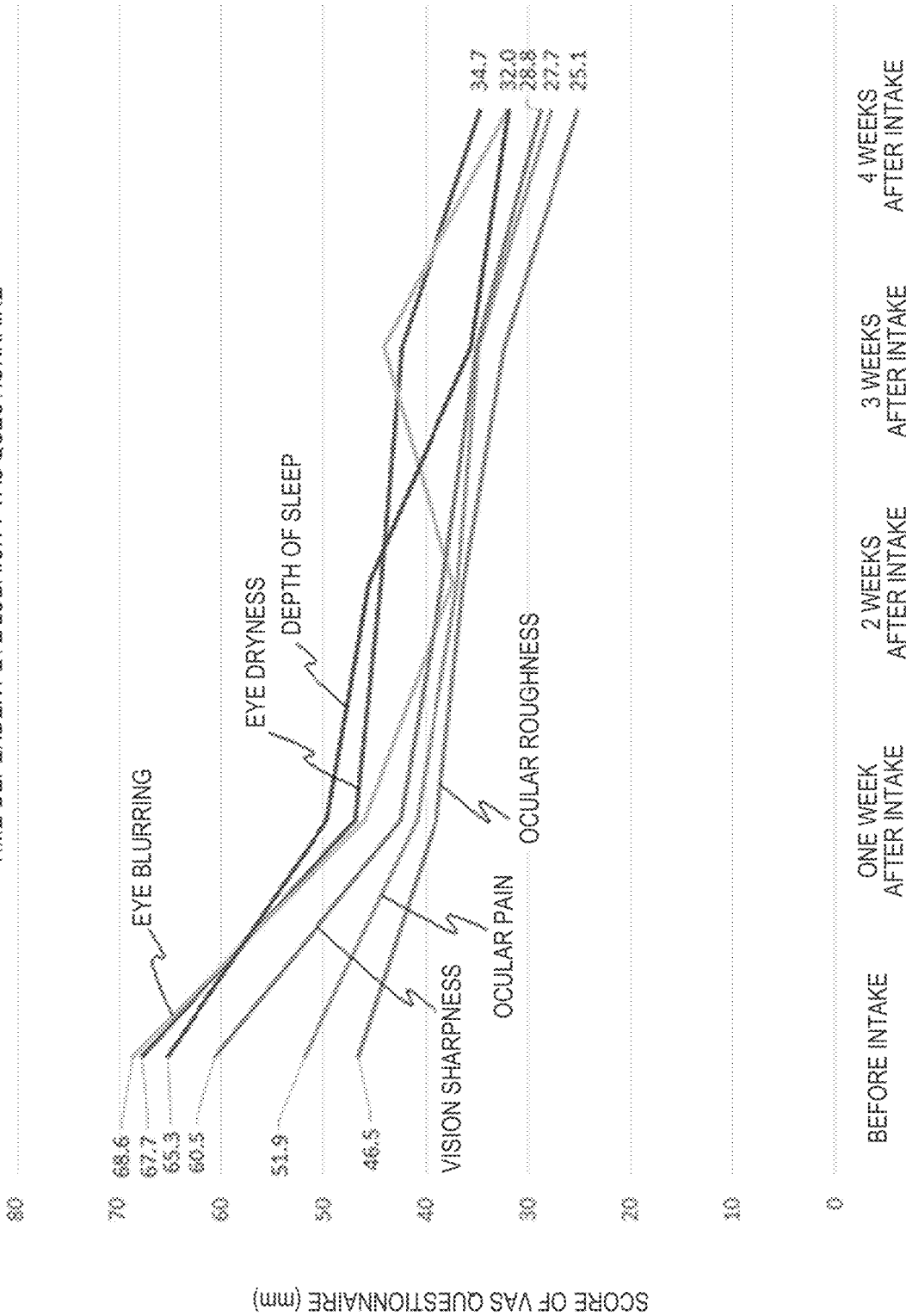

METHOD FOR IMPROVING EYE CONDITIONS

FIELD OF THE INVENTION

The present invention relates to a method for improving eye conditions using a protease-degraded product of a comb.

BACKGROUND OF THE INVENTION

In the modern society, there are a flood of factors, such as long-term personal computer work, drying by an air conditioner and wearing a contact lens, which worsen eye conditions, and there is an increasing number of patients appealing eye dryness, fringing, pain, razor and vision blur. Such deterioration of eye conditions significantly reduces quality of life, and if the condition is left untreated to cause aggravated conditions, damage may occur in the cornea and conjunctiva, leading to body disorders such as headache and dizziness. Consequently, when eye conditions have worsened, it is important to perform an early treatment to improve the eye conditions.

Regarding pharmaceutical preparations for improving eye conditions, generally employed are ophthalmic solutions to he directly administered to eyes, artificial tears, hyaluronic acid formulations, drugs that promote the production or secretion of mucin, or liquid pharmaceutical preparations containing anti-inflammatory agents such as adrenal corticosteroids (for example, see PTL 1). A process for administration of such an ophthalmic solution is such that, with hands clean and taking care to pull the lower eyelid of the eyepiece down while preventing the tip of the eye drop container from touching the eyelash or eyelid, about one drop of an eye lotion is dropped to the eye, then the eye is lightly closed, and thereafter the excessive eye lotion having adhered to the eye lid or the skin is rubbed off with a tissue.

SUMMARY OF THE INVENTION

As described above, for a medical treatment for improving an eye condition, generally used are eye-drops. However, eye-drops have problems that a complicated procedure is necessary and a patient burden is great. When patients are children, they may have some fear of drug entering the eye, and may move or cry, and in such cases, eye-drop administration could not be attained well. Further, after eye-drops are once opened, microbes may enter them to readily propagate therein, and therefore care is needed in that, after opened, eye-drops must be stored in refrigerators, or the expiration date after opening must be protected, but it is difficult to thoroughly protect such cautions. Furthermore, for preventing proliferation of microbes, a preservative chemical is generally added to eye-drops, and there is a risk that the preservative chemical may cause corneal epithelium disorder or allergy.

As described above, eye-drops are difficult to handle, and it is desired to develop a therapeutic agent in an administration type that facilitates intake or storage and can improve eye conditions. However, up to now, no oral medicine is known which can be administered by mouth and can exhibit a function of effectively improving eye conditions.

Accordingly, for the purpose of solving the problems associated with the conventional technology, the present inventors have made further investigations intending to provide a composition capable of improving eye conditions by oral administration. Also the inventors have made investigations intending to provide a production method for producing such a composition at low cost.

As a result of assiduous studies for solving the above-mentioned problems, the present inventors have found for the first time that, by orally administering a degradation product prepared by degrading combs with a protease, eye conditions can be improved. With that, the present inventors have found that, utilizing the effects of the protease degradation product of combs, there can be provided an orally-administrable improvers for eye conditions that are more readily handleable than eye-drops. The present invention has been proposed based on these findings, and specifically has the following constitution.

The present invention provides a method for improving an eye condition comprising orally administering to human, a degradation product containing an ethanol-soluble component, which is obtained by degrading a comb with a protease and removing a solid.

The present invention also provides an eye condition improver for oral administration to human, which contains a degradation product containing an ethanol-soluble component obtained by degrading a comb with a protease and removing a solid.

The eye condition improvement includes one or more selected from the group consisting of vision enhancement, intraocular pressure reduction, vision sharpening, sleep improvement, dry eye improvement and ocular pain suppression. For example, the eye condition improvement is one or more selected from the group consisting of vision enhancement, intraocular pressure reduction, vision sharpening and sleep improvement. For example, the eye condition improvement is dry eye improvement. For example, the eye condition improvement is ocular pain suppression.

The ethanol-soluble component in the degradation product preferably accounts for 10% by mass or more of all the solid content. The degradation product preferably contains a free amino acid.

When the degradation product produced by degrading a comb with a protease, which is used in the present invention, is orally administered, eye conditions can be effectively improved. Utilizing the effects of the degradation product, an orally-administrable eye condition improver can be realized. In addition, the eye condition improver of the present invention can be produced at low cost.

BRIEF DESCRIPTION OF THE DRAWING

The drawing is a graph showing time-dependent response results of VAS Questionnaire relating to subjective symptoms of eye conditions before intake of protease degradation product-containing capsules of the present invention and after intake thereof for a predetermined period of time.

DETAILED EXPLANATION OF INVENTION

The present invention is described in detail hereinunder. The description of the constitutive elements of the invention given hereinunder is for some typical embodiments or examples of the invention, to which, however, the invention should not be limited. In this description, the numerical range expressed by the wording "a number to another number" means the range that falls between the former number indicating the lower limit of the range and the latter number indicating the upper limit thereof.

[Eye Condition Improver]

The eye condition improver of the present invention is a composition containing a degradation product obtained by degrading a comb with a protease and removing a solid. The degradation product contains an ethanol-soluble component existing after degrading a comb with a protease.

The "comb" for use in the present invention is a mucous coronary protrusion on the head found in some birds of the family Phasianidae such as chicken. The kind of the comb for use in the present invention is not specifically limited but is preferably a cock's comb. The comb contains at least a protein and a hyaluronic acid, and therefore, a degradation product obtained by degrading such a comb with a protease is a composition containing at least a degradation product of a protein degraded with a protease and a low-molecular hyaluronic acid. The degradation product may contain an undegraded protein (a protein originally contained in the comb before protease addition) and any other comb-derived component.

The kind of the protease for use in the present invention is not specifically limited. Any protease usable for ordinary proteolysis is usable here. Specifically, an endopeptidase or an exopeptidase is usable, and the active site may be any of serine, cystine, metal, aspartic acid, etc. Plural proteases may be mixed and used here. As a preferred protease, for example, a pronase may be used.

The protein-degraded product contained in the degradation product includes a protein, a peptide and a free amino acid having a lower molecular weight than that of the undegraded protein, and these may exist in the degradation product as mixed therein.

Preferably, the degradation product contains a free amino acid. The free amino acid that the degradation product contains may be a free amino acid as a protein-degraded product, or a free amino acid naturally contained in the comb before protease addition thereto. In the degradation product from a comb with a protease, amino acids such as isoleucine, β-aminoisobutyric acid, alanine, phenylalanine, aspartic acid, cystine and tyrosine are contained in a relatively high content, and in addition to these, other various kinds of amino acids are contained therein.

The total protein amount in the degradation product is preferably 2 to 40% by mass as a ratio by mass relative to the total amount of the degradation product, more preferably 4 to 28% by mass, even more preferably 8 to 16% by mass. The total free amino acid amount in the degradation product is preferably 5 to 30% by mass as a ratio by mass relative to the total amount of the degradation product, more preferably 10 to 25% by mass, even more preferably 12 to 20% by mass. It is considered that, when the total protein amount and the total free amino acid amount in the degradation product each fall within the above range, the eye condition improver containing the degradation product can effectively act to early improve eye conditions.

In the present specification, "the total protein amount" means a total protein content determined by a Lowry method, and the "total free amino acid amount" means a total amount of free amino acids determined by a Ninhydrin method.

The hyaluronic acid that the degradation product contains is a degradation product of a hyaluronic acid. The hyaluronic acid that the degradation product contains is preferably all a hyaluronic acid having a molecular weight of 110,000 or less. In particular, a low-molecular hyaluronic acid having a molecular weight of 5000 or less can readily penetrate into the depth of a living body, and is therefore preferred since such a low-molecular hyaluronic acid can effectively attain the effects on living bodies.

The low-molecular hyaluronic acid that the degradation product contains is a low-molecular hyaluronic acid obtained by degrading the hyaluronic acid originally contained in the comb as a raw material for the degradation product (hereinafter referred to as "raw material-derived hyaluronic acid"). Preferably, the degradation of the raw material-derived hyaluronic acid is carried out along with protease treatment. It can be carried out by pH control or with a hyaluronidase. Also a low-molecular hyaluronic acid can be produced by utilizing self-digestion with substances originally contained in combs. However, from the viewpoint of effectively attaining the effect of hyaluronic acid on living bodies, it is preferable that the hyaluronic acid keeps the constituent unit, that is, the degradation does not reach glucuronic acid and N-acetylglucosamine. Specifically, the content of N-acetylglucosamine in the eye condition improver is preferably 0.01% by mass or less, most preferably 0% by mass relative to the total amount of the eye condition improver.

In the present specification, the "N-acetylglucosamine amount" is an N-acetylglucosamine content determined by a Morgan-Elson method.

The hyaluronic acid that the degradation product contains is mainly a low-molecular hyaluronic acid having a molecular weight of 380 to 5000. Preferably, the low-molecular hyaluronic acid accounts for 95% by mass or more of the hyaluronic acid contained in the degradation product. Also preferably, a hyaluronic acid having a molecular weight or more than 11000 is not detected in the degradation product (for example, the content of such a hyaluronic acid is preferably 0.5% by mass or less, for example, 0.1% by mass or less, preferably 0, and a hyaluronic acid having a molecular weight of more than 100,000 and a hyaluronic acid having a molecular weight of more than 500,000 are not contained). A molecular weight of 380 to 5000 corresponds to about 1 to 14 as the recurring unit number of a hyaluronic acid. The content of the low-molecular hyaluronic acid having a molecular weight of 380 to 5000 in the eye condition improver is preferably 5% by mass or more relative to the total amount of the eye condition improver, more preferably 7% by mass or more, even more preferably 10% by mass or more, and is preferably 25% by mass or less, more preferably 20% by mass or less. Of the low-molecular hyaluronic acid, preferably, the main component is a low-molecular hyaluronic acid having a molecular weight of 1520 to 5000, also preferably, the proportion of a low-molecular hyaluronic acid having a molecular weight of 1520 to 5000 is 60% by mass or more of all the amount of the low-molecular hyaluronic acid having a molecular weight of 380 to 5000, more preferably 70% by mass or more, even more preferably 75% by mass or more. With that, it is considered that the eye conditioner improver can effectively act to improve eye conditions in the early stages. The molecular weight and the mass ratio of the low-molecular weight hyaluronic acid can be determined by high-performance liquid chromatography using polyethylene glycol as a molecular weight marker. The content of the hyaluronic acid in the degradation product is 60% by mass or less. The content of the free amino acid in the degradation product and the eye condition improver is preferably 10 to 60% by mass of the content of the hyaluronic acid therein, more preferably 20 to 40% by mass, even more preferably 25 to 35% by mass.

The properties of the degradation product produced by degrading a comb with a protease may differ depending on the kind of the comb, the condition of the living subject from which the comb has been collected and the kind of the protease, but in general, the degradation product is liquid, and is further a mucilaginous liquid. The degradation product can be, directly as it is, the eye condition improver of the present invention, or can be appropriately purified and combined with any other component to be the eye condition improver of the present invention. By purifying the degradation product, an eye condition improver having a higher effect of improving eye conditions can be provided. The liquid eye condition improver can be administered as a drink-type internal agent. In the case where the degradation product is dried by lyophilization and then ground, a powdery eye condition improver can be provided. A powdery eye condition improver can be used as an internal agent, directly as it is, or after combined with any other component, or can also be processed into tablets or capsules, or a desired solvent or dispersant can be added thereto to be liquid, and can be administered as a drink-type internal agent. The liquid eye condition improver and the liquid prepared by adding the powdery eye condition improver to a solvent or a dispersant can also be used as an external agent as dye-drops, but are preferably used as an internal agent from easiness in dosing and storage.

As in the above, the eye condition improver of the present invention can be in any form so far as it can exhibit an eye condition improving effect, and is, in particular, preferably used as an oral administration-type form. For example, the eye condition improver can be used as medicines (pharmaceutical composition) explicitly describing the efficacy, quasi-drugs, functional foods (including supplementary foods, healthy foods, candies, and chewing gums), functional drinks (including jelly-type drinks, and solid-containing fluid drinks), and supplements. It is interpreted that these use embodiments are within the scope of the "eye condition improver" of the present invention.

The eye condition improver of the present invention can contain any other various components than the above-mentioned degradation product. For example, in the case where the eye condition improver contains an excipient, the amount of the components therein, such as a toral protein mass, a total free amino acid amount and the low-molecular hyaluronic acid, can be controlled by controlling the blending ratio of the degradation and the excipient. As an embodiment of an easily storable eye condition improver, there can be mentioned a mixed powder prepared by grinding a freeze-dried degradation product followed by diluting the resultant powder with an excipient. The excipient is not specifically limited but is preferably dextrin. Preferably, the dilution ratio with an excipient is 2 to 10 times by mass, more preferably 2 to 7 times by mass, even more preferably 3 to 5 times by mass.

When taken, the eye condition improver of the present invention exhibits the effect of improving eye conditions. Namely, when the eye condition improver of the present invention is orally taken, the components thereof are absorbed by the gastrointestinal tract to reach and moisturize the eye tissue, for example, conjunctiva and cornea to thereby restore the function of eyes. With that, dry eye symptoms and eye conditions such as vision, intraocular pressure, ocular pain, and visibility can be effectively improved, and appearance of physical symptoms such as headache and spatula associated with eye symptoms can also be suppressed. Here, the eye condition improver of the present invention uses a comb of a living body tissue and a mild reactive enzyme, and has advantages of high safety and easy usability as a peroral internal agent.

The dose of the eye condition improver of the present invention can he appropriately determined in consideration of the age and the body weight of the person targeted for administration, and the dosage form.

For example, in the case where the eye condition improver of the present invention is orally administered as an internal medicine, the dosage thereof is preferably 80 to 2000 mg/adult standard body weight/day, and is appropriately administered as divided into 2 to 3 parts a day. The dosage as the protease degradation product is preferably 1 to 1500 mg/adult standard body weight/day.

[Production Method for Eye Condition Improver]

Next described is a production method for the eye condition improver of the present invention.

A production method for the eye condition improver of the present invention includes an enzyme treatment step of degrading a comb with a protease, and a solid removing step of removing a solid after the enzyme treatment step. The production method for the eye condition improver of the present invention can further include, after lyophilization after the solid removing step, a grinding step of grinding the product to obtain a ground matter.

Further as needed, the production method for the eye condition improver of the present invention can include any other step. For example, before the enzyme treatment step, the method can include a chipping step of chipping a comb into small pieces. The method can further include a purification step of purifying the product from which a solid has been removed. The production method for the eye condition improver of the present invention is described in detail hereinunder.

First, combs to be a raw material are prepared. The combs can be collected from cocks or can also be collected from other birds of the Phasianidae, but are preferably cock's combs as easily available. Combs can be used irrespective of the gender and age of the collection source. However, it is preferable that the combs are subjected to protease decomposition not taking time so much after collection. When the combs are subjected to protease degradation after taking time, it is preferable that the combs are freeze-dried and then thawed before use.

In protease degradation of a comb, preferably, the comb is processed in a chipping step of chipping it, and then the resultant comb pieces are brought into contact with a protease-containing solution. The comb is preferably chipped into pieces of 0.5 cm square or more, more preferably 0.7 cm square or more, even more preferably 0.9 cm square or more. If too much chipped or minced, water may excessively flow out of the resultant pieces, unfavorably.

Next, combs are degraded with the protease in an enzyme treatment step. Regarding the description of the protease for use in the production method of the present invention, reference can be made to the description of protease in the section of "Eye Condition Improver" given hereinabove. The enzyme treatment step varies depending on the kind of the protease. For example, it is preferable that a solution (enzyme solution) such as an aqueous solution where a protease has dissolved is added to combs, and then left as such for a predetermined period of time. Here, preferably, the enzyme solution has a pH of 5.0 to 10.0 (for example, 5.0 to 6.7), the processing temperature is preferably 40 to 60° C., and the processing time is preferably 0.5 to 3.0 hours. Also preferably, the enzyme treatment is carried out while combs to which an enzyme solution has been added are shaken. In one embodiment of the present invention, the product obtained after protease treatment has a Brix value of, for example, 5.2 to 7.2 (preferably 5.7 to 6.7, and a solid concentration of, for example, 4 to 8% by mass (preferably 5 to 7% by mass).

Preferably, treatment for depolymerization of combs is not carried out in a separate step before protease treatment of combs. For example, it is preferable that a step of previously depolymerizing hyaluronic acid contained in combs is not carried out before protease treatment.

Next, a solid is removed from the product obtained in the manner as above. Solid removal is carried out, for example, by a method of filtration. Solid removal can also be carried out by centrifugation. A liquid substance after solid removal contains an ethanol-soluble component. The ethanol-soluble component accounts for 10% by mass or more of the entire solid content contained in the liquid substance (solid component after solvent removal), and can be 30% by mass or more, or can be 50% by mass or more, or can be 70% by mass or more. The liquid substance thus obtained can be used directly as it is as a degradation product in the eye condition improver, and can also be used in the eye condition improver after processed in a grinding step to be mentioned below.

In the grinding step, the liquid substance obtained in the solid removal step is freeze-dried and then ground to give a powdery degradation product. For freeze-drying and grinding, any known grinding condition for a freeze-dried powder can be employed. The resultant powder degradation product can be used as the eye condition improver of the present invention, directly as it is, or can be appropriately purified and combined any other component such as an excipient to be the eye condition improver of the present invention. The hyaluronic acid content in the eye condition improver of the present invention is 25% by mass or less of the entire amount of the eye condition improver, and is preferably 15% by mass or less.

The eye condition improver of the present invention can be produced in such an extremely simple process. Consequently, using the production method of the eye condition improver of the present invention, a highly-useful eye condition improver can be provided at low cost.

By further purifying the liquid product after solid removal or the powdery product after powdering treatment, there can be provided an eye condition improver of which the effect of improving eye conditions is higher.

[Use of Eye Condition Improver]

As described above, the eye condition improver of the present invention exhibits an effect of improving eye condition by oral administration to human. Here, "eye condition" in the "eye condition improver" means all the conditions relating to eyes, and includes, for example, eye symptoms and somatic symptoms appearing owing to dry eye (dry eye symptoms), vision, intraocular pressure, ocular pain, vision sharpness, and sleep condition. "Eye condition improving effect" means an effect of improving such eye conditions, and includes, for example, relief or resolution of dry eye symptoms, vision enhancement, intraocular pressure reduction, ocular pain suppression or resolution, vision sharpening, and sleep depth improvement. Consequently, the eye condition improver of the present invention can be effectively used as a dry eye improver, a vision enhancer, an intraocular pressure reducing agent, an ocular pain suppressing agent, a vison sharpening agent and a sleep improver. The dye condition improver can also be used as drug compositions, foods or drinks by as a combination of uses of two or more kinds selected from these agents. The eye condition improver as an internal agent can optionally contain any other various components except the above-mentioned degradation product and excipient. For example, vitamins, vegetable powder, minerals, yeast extracts, colorants and thickeners can be added as needed. The kind of these components is not specifically limited, and the content thereof can be appropriately controlled within a range capable of sufficiently exhibiting the intended function. In one preferred embodiment of the present invention, the eye condition improver of the present invention is perorally administered to a human having dry eye symptoms. In one preferred embodiment of the present invention, the eye condition improver of the present invention is perorally administered to a dry eye patient. In one preferred embodiment of the present invention, the eye condition improver of the present invention is perorally administered to a human having an impaired vision. In one preferred embodiment of the present invention, the eye condition improver of the present invention is perorally administered to a human having a high intraocular pressure. In one preferred embodiment of the present invention, the eye condition improver of the present invention is perorally administered to a human having a poor vision sharpness. In one preferred embodiment of the present invention, the eye condition improver of the present invention is perorally administered to a human suffering from imperfect sleep. In one preferred embodiment of the present invention, the eye condition improver of the present invention is perorally administered to a human having an ocular pain.

For example, even when a hyaluronic acid having an average molecular weight of 6000 is perorally administered to a dry eye patient, any significant eye condition improving can not be attained. On the other hand, when the eye condition improver of the present invention containing an ethanol-soluble component is perorally administered, an extremely excellent eye condition improving effect can be attained.

EXAMPLES

The present invention is described more specifically with reference to Examples given below. The materials, the ratio thereof and the operations in the following Examples may be appropriately varied not overstepping the scope and the spirit of the present invention. Accordingly, the range of the present invention should not be interpreted limitatively by the specific examples shown below.

Component analysis of the compositions produced in this Example was carried out according to the following methods.

(1) Measurement of Water Content

One g of the composition was heated and dried at 105° C. for 3 hours, and the constant weight thereof was measured with a precision balance to quantify the water content thereof.

(2) Total Nitrogen Determination

The total nitrogen was quantitatively determined according to a semimicro-Kjeldahl method based on an AOAC method.

(3) Free Amino Acid Determination and Amino Acid Composition Analysis

The total free amino acid amount was quantified according to a ninhydrin method. For quantification, a calibration curve of leucine as a standard amino acid was formed and used. The composition of the free amino acid was analyzed using an amino acid automatic analyzer (manufactured by Hitachi Limited, L-8500 Model) equipped with a column for bioanalysis. In the analysis, 50 mg of the composition was dissolved in distilled water, dried into solid under reduced pressure using a rotary evaporator (60° C.), then eluted with 5 mL of 0.02 N hydrochloric acid, and filtered through filter paper and then through a germ-free filter, and 50 μL of the resultant filtrate was used as an analysis sample.

(4) Protein Determination

The total protein amount was determined according to a Lawry method. A bovine serum albumin was used for forming a standard calibration curve.

(5) N-acetyl-D-glucosamine Determination

The N-acetyl-D-glucosamine content was determined according to a Morgan-Elson method.

(6) Glucosaminoglycan Determination

The sample was analyzed through colorimetry according to a 2-nitrophenylhydrazine coupling method. For standard calibration curve formation, comb-derived sodium hyaluronate (manufactured by Wako Pure Chemical Corporation, HARC) and Streptococcus zooepidemicus-derived sodium hyaluronate (manufactured by Wako Pure Chemical Corporation, HASZ) were used.

(7) Measurement of Molecular Weight of Low-Molecular Hyaluronic Acid

The molecular weight of hyaluronic acid was estimated through high-performance liquid chromatography (by Shimadzu Corporation) equipped with a differential refractometer (manufactured by Shimadzu Corporation, RID-10A Model). Columns of TSKgel G-2, 500PW$_{XL}$ (7.8 mm ID×30 cm) were used, and water was used as a mobile phase at a flow rate of 1 ml/min for analysis. As a molecular weight marker, four types of polyethylene glycol having a molecular weight of 400, 1000, 2000 or 6000 (manufactured by Aldrich Corp.) were used. The constituent weight ratio of each low-molecular hyaluronic acid was analyzed through high-performance liquid chromatography using samples of the pharmaceutical composition or dextrin alone, in which the peak area of dextrin was detracted from the peak area of the composition to determine the constituent weight ratio.

[Production Example]

One kg of freshly collected cock's combs were cut into small pieces of about 1 cm square, and thermally sterilized by steaming at 100° C. Food-derived enzymes mainly containing a protease were added to the small pieces and reacted at 45° C. for 1.5 hours, and then stirred and homogenized. Subsequently, rough solid fragments were removed by filtration to give a liquid degradation product (hereinafter referred to as "protease degradation product"). The protease degradation product had a pH of 6.5, a Brix value of 6.20 and a solid concentration of 5.91% by weight. The protease degradation product was freeze-dried and ground to be a freeze-dried powder of protease degradation product (composition 1). Dextrin in an amount of 3 equivalent times (as a ratio by mass) was added to the freeze-dried powder of protease degradation product to give a dextrin-added freeze-dried powder (composition 1').

[Component Analysis of Composition]

The produced composition 1' was analyzed for the constituent components thereof according to the above-mentioned method. The content of general components analyzed is shown in Table 1, the composition of free amino acids is shown in Table 2, and the analysis results of molecular weight of low-molecular hyaluronic acids are shown in Table 3. In Tables 1 to 3, "%" is "% by mass".

TABLE 1

| General Components | |
|---|---|
| | % |
| Water | 2.2-2.6 |
| Nitrogen | 3.84 |
| Total Protein | 3.04 |

TABLE 1-continued

| General Components | |
|---|---|
| | % |
| Free Amino Acid | 4.08 |
| N-acetylglucosamine | 0 |
| Dextrin (for food additive) | 75.0 |

TABLE 2

Free Amino Acid Composition

| Amino Acid | Content % | Amino Acid | Content % |
|---|---|---|---|
| ρ-serine | 1.71 | Cystine* | 2.78 |
| Taurine | 3.30 | Leucine* | 2.26 |
| Aspartic Acid* | 2.94 | Isoleucine* | 6.27 |
| Threonine* | 1.30 | Tyrosine* | 2.65 |
| Serine* | 2.20 | Phenylalanine* | 3.30 |
| Glutamic Acid* | 2.18 | β-aminoisobutyric Acid | 5.45 |
| Glutamine | 0.48 | Ornithine | 1.05 |
| Sarcosine | 1.81 | Lysine* | 1.17 |
| Glycine* | 2.26 | 1-Methylhystidine | 0.78 |
| Alanine* | 3.52 | Anserine | 1.92 |
| Citrulline | 0.92 | Arginine* | 1.93 |
| α-Aminobutyric Acid | 2.18 | Identified Total Amino Acids | 57.36 |
| Cystine* | 1.03 | Unknown Amino Acids | 42.64 |
| Methionine* | 1.97 | | |

*Protein composition amino acid

TABLE 3

Estimated Molecular Weight, Constituent Unit Number and Constituent Weight Ratio of Low-Molecular HA

| | Peak No.123 | | | | |
|---|---|---|---|---|---|
| | 1 | 2 | 3 | 4 | 5 |
| Estimated Molecular Weight | 5,000 | 1,520 | 1,140 | 760 | 380 |
| Constituent Unit Number | 13-14 | 4 | 3 | 2 | 1 |
| Constituent Weight Ratio (%) | 33 | 47 | 10 | 6 | 4 |

As shown in Table 2, among the free amino acids contained in the composition 1' the content of isoleucine and β-aminoisobutyric acid was high, and then, alanine, phenylalanine, aspartic acid, cystine and tyrosine were contained much.

As shown in Table 3, the composition 1' contained five types of low-molecular hyaluronic acids each having an estimated molecular weight of 5000, 1520, 1140, 760 and 380. When the molecular weight of one recurring unit of hyaluronic acid is about 400, the recurring unit number of each low-molecular hyaluronic acid is 13 to 14, 4, 3, 2 and 1 in that order from the largest molecular weight, and the mass ratio was 33%, 47%, 10%, 6% and 4%. Accordingly, it is known that the main components of the low-molecular hyaluronic acids are two components of a 4-molecular component having a molecular weight of about 1520, and a 13 to 14-molecular component having a molecular weight of about 5000. The content of the low-molecular hyaluronic acids having a molecular weight of 380 to 5000 in the composition 1' was 13.4% by mass relative to the total amount of the composition 1'.

[Preparation of Composition-Containing Capsule Formulation]

A dextrin-added freeze-dried powder (composition 1') prepared by adding dextrin to a freeze-dried, protease-degraded product powder in an amount of 3 times by equivalent (ratio by mass) was encapsulated in gelatin capsules to prepare a capsule formulation (hereinafter referred to as "protease-degraded product-containing capsules"). At this time, the amount of the freeze-dried, protease-degraded product powder that the capsules contained was 150 mg/capsule.

[Evaluation of Effect of Composition]

The effect of the freeze-dried powder of protease degradation product produced in Production Example was evaluated by panelists, healthy 12 men and women (6 men, 6 women) who were aware of daily dry eye and eyestrain. The age range of the panelists was 20 or more and less than 60. Specifically, before start of intake, each panelist was subjected to an eye lubricity test mentioned below. Subsequently, the panelists took protease degradation product-containing capsules, 4 capsules twice a day along with water or tepid water, and from the start of intake, after one week, after 2 weeks, after 3 weeks and after 4 weeks, the panelists were subjected to the same test. Here, the dosage of the capsule preparation corresponds to 1200 mg=600 mg as one intake a day×two times, of the freeze-dried powder of protease degradation product.

In the eye lubricity test, the panelists responded to specific items of DEQS (dry eye related quality of life score) by the Dry Eye Study Group, subjective symptom-related somesthetic VAS (visual analogue scale) questionnaire, and anti-aging QOL common medical questionnaire by the Japanese Society of Anti-Aging Medicine, and were subjected to measurement of BUT (tear film break-up time) and subjected to an eyesight test and an intraocular pressure test. The test results before the start of intake and the test results after 4 weeks from the start of intake are shown in the following Tables 4 to 6, and a graph of the time-dependent response results of VAS Questionnaire is shown in the drawing.

Here, the score of the dry eye QOL questionnaire shown in Table 4 is QOL scores calculated based on the panelists' responses. QOL scores range 0 to 100, and a larger value means a higher severity level of dry eye symptoms, and indicates that the symptoms have a greater influence on the daily life and the mental aspect. The scores of the VAS questionnaire shown in Table 4 indicate a distance (mm) from the left end on a 100-mm line segment on which the panelists marked their own conditions in such a manner that the left end is the best condition (with no symptom) and the right end is the worst condition (one's worst-symptom ever). A larger score means a highest subjective symptom in every evaluation item.

In the physicochemical test shown in Table 5, test paper for Flores eye examination (by AYUMI Pharmaceutical Corporation) was used for detection of tear film; in the eyesight test, a space saving chart (ssc-370 Type D, by NIDEK Corporation) was used; and in the intraocular pressure test, a multifunction refractometer (MR-6000, by TOMEY Corporation) was used. In Table 5, a perforated card method was employed for decision of "superior eye" (dominant eye) and "non-superior eye" (non-dominant eye).

The scores of antiaging QOL common medical questionnaire shown in Table 6 are in five stages of the physical symptom of each item, "1: No, not at all", "2: Yes, but little", "3: Yes, a little", "4: Yes, average", and "5: Yes, highly".

The values shown in Tables 4 to 6 and the drawing are average values of all the panelists. The significant level in each evaluation item is in a two-sided test for the variation after 4 weeks from the start of intake relative to before the start of intake, 5% (P value=0.05).

TABLE 4

| Subjective Symptom Test Item | | before Intake (average value) | 4 Weeks after Intake (average value) | P value of Variation |
|---|---|---|---|---|
| Dry Eye QOL Questionnaire | QOL Score | 52.40 | 23.60 | 0.002 |
| VAS questionnaire | Ocular Dryness | 67.70 | 34.70 | 0.001 |
| | Ocular Roughness | 46.50 | 25.10 | 0.021 |
| | Ocular Pain | 51.90 | 27.70 | 0.017 |
| | Ocular Bleariness | 68.60 | 32.00 | 0.002 |
| | Vision Sharpness | 60.50 | 28.80 | 0.007 |
| | Depth of Sleep | 65.30 | 31.90 | 0.013 |

Before/After Comparison

TABLE 5

| Physicochemical Test Item | | before Intake (average value) | 4 Weeks after Intake (average value) | P value of Variation |
|---|---|---|---|---|
| Tear Film Breaking Time (BUT) | non-dominant eye (sec) | 3.20 | 5.50 | 0.001 |
| | average of both eyes (sec) | 3.63 | 5.54 | 0.023 |
| Vision Test | corrected (average of both eyes) | 1.38 | 1.58 | 0.044 |
| Intraocular Pressure Test | dominant eye | 13.02 | 11.74 | 0.014 |
| | non-dominant eye | 12.96 | 11.66 | 0.015 |
| | average of both eyes | 12.99 | 11.70 | 0.004 |

Before/After Comparison

TABLE 6

| Antiaging QOL Common Medical Questionnaire (physical symptom test item) | before Intake (average value) | 4 Weeks after Intake (average value) | P value of Variation |
|---|---|---|---|
| Eye Tired | 4.3 | 2.9 | 0.003 |
| Eye Blurred | 3.4 | 2.2 | 0.006 |
| Eye Pam | 3.1 | 1.8 | 0,006 |
| Dizzy | 2.3 | 1.3 | 0.016 |

Before/After Comparison

As shown in Tables 4 to 6, when comparison was made between before the start of intake of protease degradation product-containing capsules and after 4 weeks from intake thereof, the dry eye subjective symptoms, the physical symptoms relating to eye condition (depth of sleep, test items shown in Table 6), the corrected eyesight and the intraocular pressure were significantly improved in 4 weeks after the intake. In addition, as shown in the drawing, the dry eye subjective symptoms were greatly relieved in one week after intake. From the above results, it is confirmed that, by oral intake of the degradation product produced by degrading combs with a protease, eye conditions can be improved.

What is claimed is:

1. A method for improving dry eye, comprising orally administering to a human in need thereof, an effective amount of a composition containing a degradation product obtained by degrading a comb with a protease and removing solids from the comb degraded with the protease, wherein;
   the degradation product contains an ethanol-soluble component in an amount of 70% by dry weight; and
   the degradation product contains a low-molecular weight hyaluronic acid having a molecular weight of 380 to 5000 in an amount of 95% by mass or more of total hyaluronic acid contained in the degradation product.

2. The method for improving dry eye according to claim 1, wherein the degradation product is a liquid product obtained by degrading a comb with a protease and removing a solid from the comb degraded with the protease, or a freeze-dried product of the liquid product.

3. The method for improving dry eye according to claim 2, wherein the liquid product or the freeze-dried product thereof contains a free amino acid.

4. The method for improving dry eye according to claim 2, wherein the degradation product is the liquid product.

5. The method for improving dry eye according to claim 2, wherein the degradation product is the freeze-dried product.

6. The method for improving dry eye according to claim 2, wherein the composition contains an excipient.

7. The method for improving dry eye according to claim 2, wherein the composition contains dextrin.

* * * * *